United States Patent [19]

Hallings et al.

[11] Patent Number: 4,878,156

[45] Date of Patent: Oct. 31, 1989

[54] QUICK RELEASE FOCUSING HANDLE FOR SURGICAL LIGHTS

[75] Inventors: Leonard L. Hallings, Rochester; Richard W. Steiner, Newark, both of N.Y.

[73] Assignee: MDT Corporation, Rochester, N.Y.

[21] Appl. No.: 319,048

[22] Filed: Mar. 6, 1989

[51] Int. Cl.[4] .............................................. F21V 33/00
[52] U.S. Cl. .................................... 362/109; 362/399; 362/804; 16/114 R; 16/DIG. 24
[58] Field of Search .... 16/114 R, DIG. 24, DIG. 25; 362/109, 399, 804, 457, 400

[56] References Cited

U.S. PATENT DOCUMENTS

| | | | |
|---|---|---|---|
| 1,605,421 | 11/1926 | Anderson | 362/109 X |
| 4,037,096 | 7/1977 | Brendgord et al. | 362/294 |
| 4,135,231 | 1/1979 | Fisher | 362/285 X |
| 4,316,237 | 2/1982 | Yamada et al. | 362/282 X |
| 4,734,832 | 3/1988 | Moriani et al. | 362/399 X |

Primary Examiner—Stephen F. Husar
Assistant Examiner—Peggy Neils
Attorney, Agent, or Firm—Trask, Britt & Rossa

[57] ABSTRACT

A replaceable focusing handle for the focusing shaft of a lighthead includes internal surfaces which register with reaction and locking surfaces of a drive post. A shield carried by the handle prevents inadvertent detachment of the handle.

14 Claims, 2 Drawing Sheets

QUICK RELEASE FOCUSING HANDLE FOR SURGICAL LIGHTS

BACKGROUND

1. Field

This invention relates to surgical lights and is specifically directed to sterile handles for maneuvering and/or focusing such lights.

2. State of the Art

Surgical lights of the type which include a plurality of individual spotlights within a housing are well known. U.S. Pat. No. 3,887,801 discloses a typical such light with a multi-beam lighthead assembly. The individual spotlights within the lighthead housing are focused by means of a synchronizing mechanism driven by a shaft extending from the housing. The focusing shaft extends approximately axially; that is, in a direction (which in normal use may be regarded as downward) approximately normal the face plate of the housing through which the individual light beams emanate.

It is important that scrubbed personnel be permitted the freedom to maneuver and focus a surgical light during an operative procedure. Thus, the focusing shaft is typically provided with a detachable sterile handle which is either disposable or resterilizable. Typical such handles are disclosed, for example, by the aforementioned U.S. Pat. No. 3,887,801 and by U.S. Design Pat. No. 289,206.

Certain other surgical lights, for example, those disclosed by U.S. Pats. Nos. 4,037,096 and 4,135,231 contain a single light source within a reflector system. Such lights are focused by means of an axially disposed sterile handle of the same general type used by multi-beam lighthead assemblies.

Even those surgical lightheads which provide no focusing capability often carry mounting posts for detachably receiving sterile handles. Without regard to the focusing capabilities of a lighthead, detachable sterilizable handles are utilized for the repositioning and maneuvering of the lighthead by scrubbed personnel. In some instances, a lighthead may be adapted to accept a plurality of disposable or sterilizable handles on focusing shafts or stationary mounting posts.

The handles in current use suffer from a number of drawbacks. Most of them require relatively cumbersome or precise manipulations to attach and detach. It often occurs that a handle becomes contaminated under circumstances which require rapid, non-interfering replacement during a procedure. Movement of the lighthead at such times is intolerable; yet, as a practical matter, such movement—or the unwelcome intrusion of support personnel—is required to effect a rapid replacement of a sterile handle. Conventionally, sterile handles connect to the focusing shaft or post by means of screw threads. Such handles are not well adapted to rapid and reliable replacement.

Another deficiency of certain of the currently available sterile handles is their lack of positive coupling to the focusing shaft or post of the lighthead assembly. It is important in practice that a rotational movement of a focusing handle in either direction effect a predictable and reliable movement of the shaft.

There remains a need for a quick-release, sterile handle element for maneuvering and/or focusing surgical lights.

SUMMARY OF THE INVENTION

This invention comprises an improved sterile (sterilizable or presterilized, disposable) handle arrangement, particularly useful for surgical (or similar) lightheads of the type which provides focusable adjustment of the light pattern projected on a work site (operating field). This disclosure will be directed primarily to such lightheads, although the handles of this invention will find application on surgical lightheads generally. The invention is generally embodied in a handle element and certain locking components external the handle element, usually associated with a drive post. The drive post is associated with the focusing shaft of the focusing mechanism of the lighthead.

The handle element is substantially hollow, with an external contact surface configured for comfortable grasping by an operator's hand. The hollow interior of the handle element may be regarded as a cavity with an entry. The entry is situated at one end of the handle and is configured to permit entry of the distal end of the drive post. The cavity is configured to contain the drive post. The drive post is typically a portion (drive post segment) of the focusing shaft.

The drive post segment, and in some instances other portions of the focusing shaft, project from the lighthead housing. The handle element and the drive post segment are mutually adapted to couple in a releasable fashion by placing the entry of the handle element over the distal end of the exposed shaft and moving the handle element in an axial direction with respect to the shaft. Certain preferred embodiments require a correct rotational alignment of the handle element with respect to the drive post to permit axial movement of the entry over the post. No other rotational motion is required to install or replace a handle element. Disengagement of the handle element is effected by finger actuation of a release mechanism, e.g., by pressing a button, and withdrawing the handle element axially from the shaft.

Internal drive surfaces of the cavity register with corresponding reaction surfaces of the drive post. Thus, rotation of the handle element in either a clockwise or a counterclockwise direction effects a corresponding rotation of the shaft to focus the light pattern produced by the lighthead. Proper registration of the structural elements providing the internal drive and reaction surfaces may require an appropriate rotational orientation of the handle element with the drive post. Such an orientation can be effected without difficulty from virtually any location without movement of the lighthead.

In a typical installation, the handle element is pushed axially onto the drive post, thereby depressing a spring-biased retaining tab. An internal locking surface is engaged by the tab when the handle element achieves its correct operational location. To release the handle element, the tab is depressed by means of finger-actuated linkage operable from a position near, but isolated from the handle element. Such isolation is provided by a shield structure integral with or otherwise associated with the handle element. The shield also isolates the hands of the scrubbed personnel contacting the handle from the non-sterile surfaces of the lighthead. As presently envisioned, the shield may comprise a structural flange circumscribing the entry of the handle element.

The drive post may be integral with the focusing shaft of the light handle, but according to some embodiments, the drive post (or in the case of non-focusing lights, a mounting post) may be provided as an adaptor element. In such instances, one end of the adaptor connects, usually axially, with structure carried by the lighthead. Representative such structure may be the distal end of the exposed portion of a focusing shaft, a threaded hole, or a threaded stud. The other end is configured to couple with the handle element as previously described.

BRIEF DESCRIPTION OF THE DRAWINGS

In the drawings, which illustrate what is presently regarded as the best mode for carrying out the invention.

DESCRIPTION OF THE ILLUSTRATED EMBODIMENT

Figure 3:
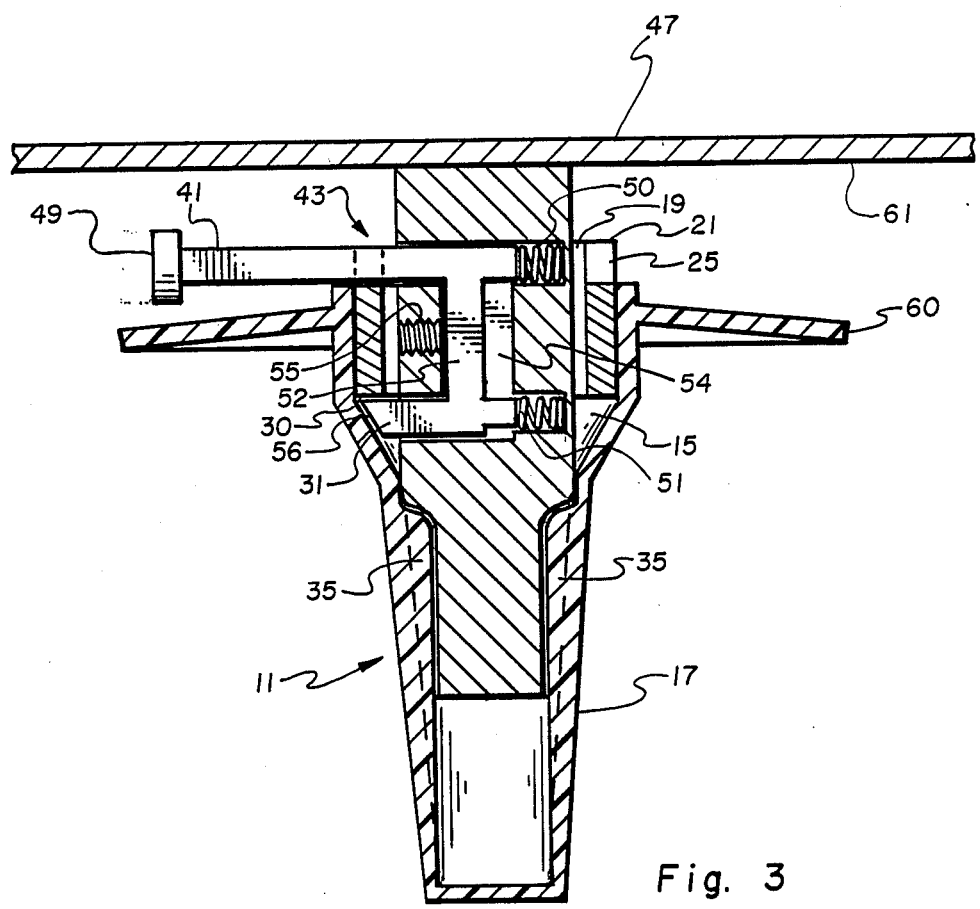
FIG. 3 is a cross-sectional view taken along the reference lines 3—3 of FIG. 2.
Figure 4:
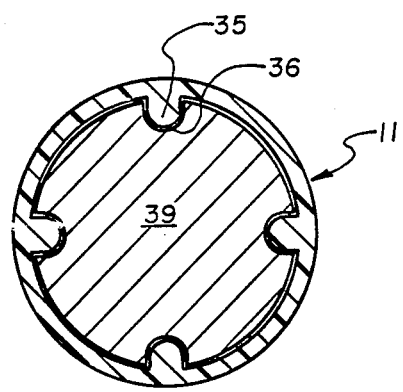
FIG. 4 is a cross-sectional view taken along the reference lines 4—4 of FIG. 2.

A handle element, designated generally 11, is formed as an approximately cylindrical solid annulus defining an internal cavity 15 and an external contact surface 17. One end of the handle element 11 carries a mouth or entry 19 into the cavity 15. As shown, entry 19 is defined by a collar 21 which carries four slots 25 at radially spaced locations separated by approximately 90°. The inner edge 30 of the collar 21 constitutes a locking surface for engagement by the tab 31 (FIG. 3). Internal ribs 35 project approximately radially inward to engage corresponding grooves 36 of a drive post 39 (FIG. 4). Each rib 35 and each groove 36 is also separated by approximately 90°, thereby providing four rotational orientations of the handle element 11 which register individual ribs 35 with corresponding grooves 36.

With the handle element installed, the ribs 35 and grooves 36 inherently align one of the slots 25 with the shaft 41 of a plunger, designated generally 43. The grooves 36 and the shaft 41 of the plunger 43 provide reaction surfaces to translate rotational motion of the handle 11, and thus ribs 35 and slots 25, to the drive post 39. The drive post 39 is shown in FIG. 2 as integral with the exposed portion 45 of the focusing shaft 46 of a lighthead 47.

The plunger assembly 43 includes, in addition to the shaft 41, a distal element 49 configured and positioned to accept finger pressure to urge the shaft 41 axially, transverse the drive post 39, against springs 50, 51. As best shown by FIG. 3, the locking tab 31 is linked to the shaft 41 by a member 52 depending through a channel 54 which permits reciprocal movement of the member 52 and thus the tab 31. Adjustment of the tab 31 position is provided by an adjustment screw 55. While tab 31 is normally biased into the engaged position shown, axial finger pressure on the distal element 45 effects disengagement, thereby permitting the axial withdrawal of the handle element 11 from the drive post 39. The tab 31 includes a ramped camming surface 56 to facilitate the installation of a replacement handle element.

Figure 2:
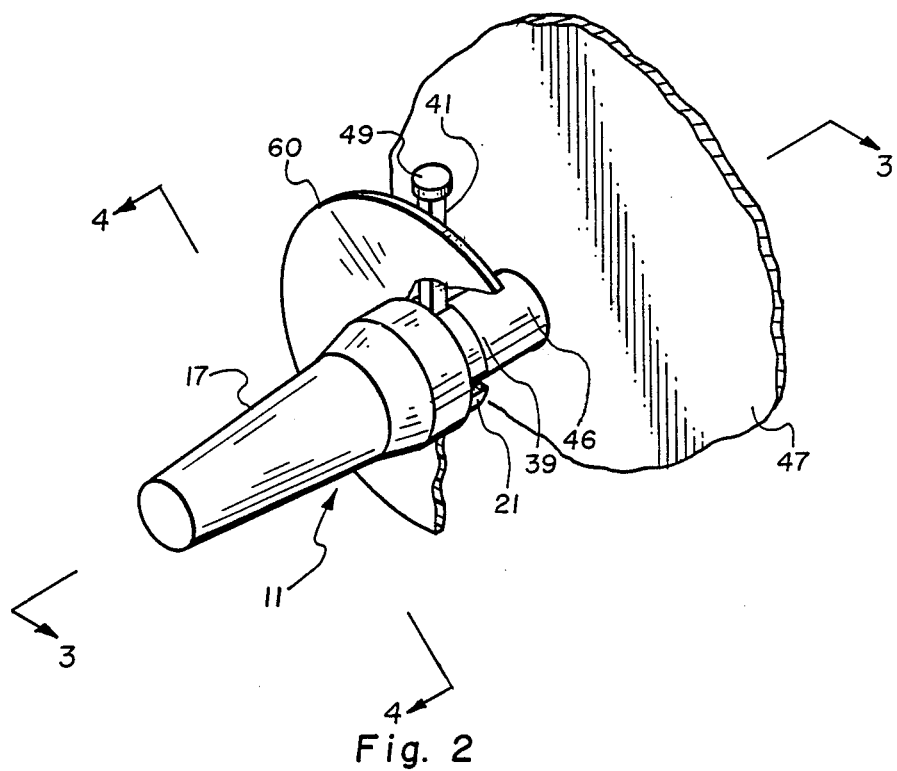
FIG. 2 is a perspective view partially broken away of an embodiment similar to that of FIG. 1 in installed condition.

A shield element 60, shown by FIGS. 2 and 3 as integral with the handle element 11, is a flange positioned between the contact surface 17 and the exposed portions of the plunger assembly 43 and adjacent surface 61 of the lighthead 47. Thus, in use, the distal end 45 may only be depressed by a purposeful effort involving a deliberate movement of the finger past the shield 60 followed by a second deliberate movement of the finger in an effective actuating direction. Ideally, the shield 60 is slightly concave as best shown by FIG. 3.

The entire handle element 11 may be constructed of materials capable of withstanding repeated sterilization procedures. While most metals are suitable from a functional standpoint, it is presently preferred to fashion the handle element 11 from heat-tolerant injection moldable or vacuum formable resinous materials.

Figure 1:
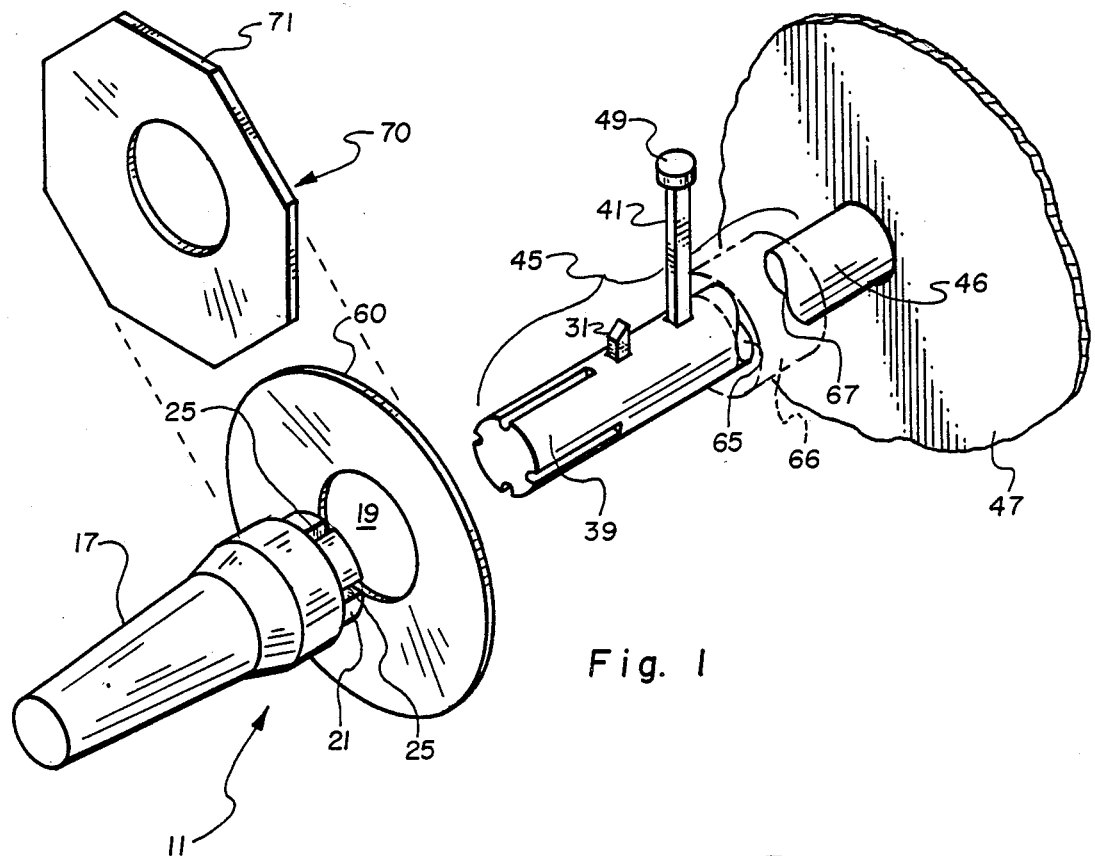
FIG. 1 is an exploded perspective view of a handle element and drive post segment of the invention.

Reference herein to details of the illustrated embodiment is not intended to restrict the scope of the appended claims. Many equivalent embodiments are within contemplation. For example, it is recognized that the shield 60 may be provided as a detachable element (as suggested by FIG. 1) to facilitate packaging and shipping. Moreover, the shield may be configured optionally as shown by the element 70 of FIG. 1. A rectilinear boundary surface 71 is preferred in that a handle with round surfaces has a tendency to roll when placed on a flat surface. The drive post 39 may be provided as a separate adaptor element (also as suggested by FIG. 1) to permit use of the invention with lightheads of various construction. In those instances, the end 65 of the drive post 39 may be adapted by any conventional mechanical means, designated generally 66, to the remainder 67 of the exposed shaft portion 45. The ribs 35 and grooves 36 illustrated may be replaced by various other reaction surface configurations. The slotted collar 21 shown, while preferred, is not regarded as an essential structural feature. The plunger assembly 43 illustrated, while presently preferred, may be replaced with other approximately equivalent "quick-release" mechanical devices.

What is claimed:

1. In a surgical light of the type in which a light source is contained within a housing in cooperable association with a focusing mechanism which includes a rotatable focusing shaft, said shaft extending from said housing, thereby to provide an exposed shaft portion with a distal shaft end, said exposed shaft portion constituting means for operating said focusing mechanism by selective alternative clockwise or counterclockwise rotation, the improvement which comprises:

a drive post segment, including said distal end, in operable association with a handle element with an external contact surface configured for grasping by a hand and a substantially hollow interior cavity with an entry at a first end of said handle element, said entry and cavity being configured to receive and contain, respectively, said drive post segment, said handle element including:

first coupling structure adapted to connect to second coupling structure associated with said drive post segment, one of said first or second coupling structure including finger actuatable release structure constituting means for disconnecting said first and second coupling structures to thereby disconnect said handle element from said drive post segment;

an internal drive surface configured to engage a corresponding reaction surface of said drive post segment, said drive and reaction surfaces cooperatively constituting means for transferring rotational movement of said handle element to said drive post segment; and a shield element circumscribing said entry between said contact surface and said release structure constituting means for isolating said release structure from a hand grasping said contact surface.

2. An improvement according to claim 1 wherein said shield element and said external contact surface are integral portions of a unitary structure.

3. An improvement according to claim 1 wherein said handle element is constructed of materials capable of withstanding repeated sterilization procedures.

4. An improvement according to claim 1 wherein said first coupling structure comprises an internal locking surface of said cavity and said second coupling structure comprises a spring-loaded retaining tab adapted to engage said locking surface.

5. An improvement according to claim 4 wherein said second coupling structure includes said finger actuatable release structure.

6. An improvement according to claim 5 wherein said finger actuatable release structure comprises a shaft element mechanically linked to said retaining tab, said shaft element extending transversely from said exposed shaft portion and carrying a distal end configured and positioned for accepting finger pressure, thereby to cause said tab to disengage said locking surface.

7. An improvement according to claim 1 wherein said drive post segment is integral with the remainder of said exposed shaft portion.

8. An improvement according to claim 1 wherein said drive post segment comprises an adaptor element with a first end constituting said distal end and a second end carrying means adapted to connect in axial alignment with mounting structure carried by the lighthead.

9. In a surgical light of the type in which a light source is contained within a housing, said housing carrying an exposed shaft portion constituting a mounting post for a removable handle, the improvement which comprises:

a mounting post segment, in operable association with a handle element with an external contact surface configured for grasping by a hand and a substantially hollow interior cavity with an entry at a first end of said handle element, said entry and cavity being configured to receive and contain, respectively, said mounting post segment, said handle element including:

first coupling structure adapted to connect to second coupling structure associated with said mounting post segment, one of said first or second coupling structure including finger actuatable release structure constituting means for disconnecting said first and second coupling structures to thereby disconnect said handle element from said mounting post segment; and a shield element circumscribing said entry between said contact surface and said release structure constituting means for isolating said release structure from a hand grasping said contact surface.

10. An improvement according to claim 9 wherein said shield element and said external contact surface are integral portions of a unitary structure.

11. An improvement according to claim 9 wherein said handle element is constructed of materials capable of withstanding repeated sterilization procedures.

12. An improvement according to claim 9 wherein said first coupling structure comprises an internal locking surface of said cavity and said second coupling structure comprises a spring-loaded retaining tab adapted to engage said locking surface.

13. An improvement according to claim 12 wherein said second coupling structure includes said finger actuatable release structure.

14. An improvement according to claim 13 wherein said finger actuatable release structure comprises a shaft element mechanically linked to said retaining tab, said shaft element extending transversely from said exposed shaft portion and carrying a distal end configured and positioned for accepting finger pressure, thereby to cause said tab to disengage said locking surface.

* * * * *